United States Patent

Rayle et al.

Patent Number: 5,959,114
Date of Patent: Sep. 28, 1999

[54] PROCESS TO CHLOROKETONES USING OXAZOLINES

[75] Inventors: Heather Lynnette Rayle, North Wales; Renee Caroline Roemmele, Maple Glen; Randall Wayne Stephens, Perkasie, all of Pa.

[73] Assignee: Rohm and Haas Company, Philadelphia, Pa.

[21] Appl. No.: 09/170,643

[22] Filed: Oct. 13, 1998

Related U.S. Application Data

[62] Division of application No. 09/058,832, Apr. 13, 1998, Pat. No. 5,859,254
[60] Provisional application No. 60/043,555, Apr. 15, 1997.
[51] Int. Cl.⁶ .................. C07D 413/04; C07D 263/12; C07D 263/14
[52] U.S. Cl. .................. 546/271.4; 548/237; 548/239
[58] Field of Search .................. 546/271.4; 548/237, 548/239

[56] References Cited

U.S. PATENT DOCUMENTS

| | | |
|---|---|---|
| 4,822,902 | 4/1989 | Carley et al. . |
| 5,304,572 | 4/1994 | Michelotti et al. . |

FOREIGN PATENT DOCUMENTS

| | | |
|---|---|---|
| 4401100 | 7/1995 | Germany . |
| WO 95/19351 | 7/1995 | Germany . |

OTHER PUBLICATIONS

Transformations of the Herbicide N–(1,1–dimethylpropynyl)–3,5–dichlorobenzamide in Soil, Roy Y. Yih, et al., *Weed Science*, vol. 18, Issue 5 (Sep.), 1970, pp. 604–607.

Identification of Metabolites of N–(1,1–dimethylpropynyl)–3,5–dichlorobenzamide in Soil and Alfalfa, Roy Y. Yih, et al., *J. Agr. Food Chem.*, vol. 19, No. 2, 1971, pp. 314–319.

*Primary Examiner*—Patricia L. Morris
*Attorney, Agent, or Firm*—Clark R. Carpenter

[57] ABSTRACT

This invention relates to a process for the preparation of an α-chloroketone compound comprising the steps of (i) cyclizing an alkynyl amide to form a 5-methyleneoxazoline

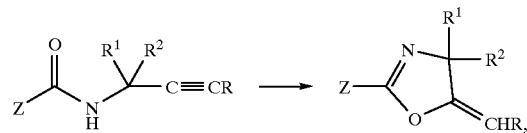

(ii) chlorinating the 5-methyleneoxazoline using trichloroisocyanuric acid to produce a chlorinated oxazoline intermediate

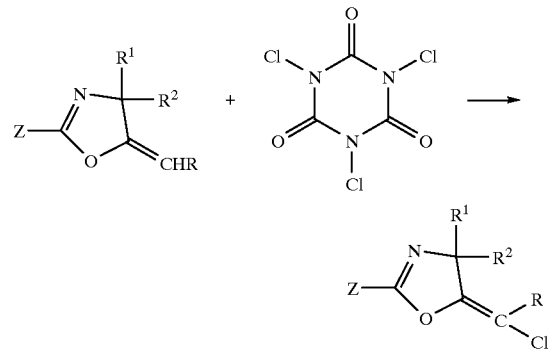

and (iii) hydrolyzing the chlorinated oxazoline intermediate with an aqueous acid to produce the desired monochloroketone

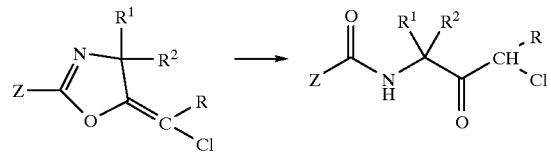

wherein
Z is alkyl or substituted alkyl, aryl or substituted aryl, heteroaryl or substituted heteroaryl or phenylene,
R is a hydrogen atom or alkyl, and
$R^1$ and $R^2$ are each independently an alkyl or substituted alkyl group, or $R^1$ and $R^2$ together with the carbon atom to which they are attached form a cyclic structure.

Additionally, when R is a hydrogen atom, a dichloroketone can be conveniently formed through adjustment of reaction conditions.

4 Claims, No Drawings

PROCESS TO CHLOROKETONES USING OXAZOLINES

This is application is a divisional application of Ser. No. 09/058,832 filed Apr. 13, 1998, now U.S. Pat. No. 5,859,254, which is based on Provisional Patent Application 60/043,555 filed Apr. 15, 1997.

This invention relates to a novel, inexpensive process to prepare 5-methyleneoxazolines from substituted alkynyl amides followed by the subsequent conversion of the 5-methyleneoxazoline to an α-chloroketone using a convenient chlorinating agent followed by hydrolysis. The resulting α-chloroketones are useful as fungicides.

There are several problems in the existing field which the present invention successfully overcomes. Previously disclosed routes to the desired 5-methyleneoxazoline from substituted alkynyl amides required the use of strong and, consequently, expensive bases such as sodium hydride or sodium amide. These bases require the use of scrupulously anhydrous conditions and are difficult to handle. Additionally, yields of the 5-methyleneoxazoline from the alkynyl amide are unacceptably low for economic viability. Other disclosed routes to the desired 5-methyleneoxazoline from substituted alkynyl amides involve treatment of the amide with silver ion in N,N-dimethylformamide. This type of procedure uses an expensive and environmentally toxic catalyst and a solvent that requires a difficult work-up and produces large volumes of organic laden aqueous waste. Still other disclosed routes employ water soluble solvents in a method to form a 5-methyleneoxazoline, but such solvents are difficult to efficiently recover and result in a process possessing undesirable cost.

The subsequent preparation of an α-chloroketone from the resulting 5-methyleneoxazoline by the known and usual methods, such as by using chlorine gas or N-chlorosuccinimide as the chlorinating agent, is also problematic because of a lack of selectivity for monochloriorination; both underchlorinated and overchlorinated ketones are typically formed in addition to the desired monochloroketone after hydrolysis of the 5-chloromethylene oxazoline. Furthermore, the use of chlorine presents hazards and an equipment expense well known to those skilled in the art.

We have discovered two convenient routes to 5-methyleneoxazolines from substituted alkynyl amides. The first requires only the use of an inexpensive base such as an aqueous solution of sodium hydroxide or sodium carbonate in the presence of an organic solvent and a phase transfer agent (PTA). The second requires only the use of an inexpensive organic or mineral acid such as oleum, an organosulfonic acid or a trihaloacetic acid in the presence of an organic solvent. Furthermore, we have identified a novel chlorination reagent; trichloroisocyanuric acid (TCIA), which chlorinates the resulting 5-methyleneoxazoline selectively to give a monochlorinated intermediate which, upon acid-catalyzed hydrolysis, affords the desired α-monochloroketone selectively and in high yield. TCIA is a high melting, easily handleable solid which can be utilized in extremely precise amounts in order to avoid under- or over- chlorination of the desired material. Although TCIA is a well known, inexpensive and commercially available compound used in the chlorination of swimming pool water and the disinfection of drinking water, its use as a convenient and selective chlorination agent for 5-methyleneoxazolines had not been disclosed before this time. An additional feature of this invention provides a convenient process for the selective formation of α,α-dichloroketones which are also useful as fungicides.

WO 95/19351 discloses the formation of aryl-5-methyleneoxazole derivatives by cyclization of an alkynyl amide in the presence of a base. However, only the use of a large amount of strong base for the cyclization is exemplified. Moreover, the use of a phase transfer agent to ameliorate the cyclization is not suggested. The use of an acid for the cyclization is also not suggested. Yih et al. in *Weed Science*, 18, 604–607 (1970) and in *J. Agr. Food Chem.*, 19, 314–317 (1971) disclose the formation of an aryl-5-methyleneoxazoline from a substituted alkynyl amide using acid, base or silver ion in an aqueous alcohol solution followed by hydrolysis to a ketone not possessing an α-chloro group. U.S. Pat. Nos. 4,822,902 and 5,304,572 disclose the formation of 5-(chloromethylene)oxazolines which are obtained by treating an alkynyl amide with chlorine. However, the use of TCIA as a chlorinating agent is not disclosed or suggested. These references, either by themselves or taken together, do not suggest the process of the present invention.

One embodiment of this invention provides a convenient process to α-chloroketories, which are useful as fungicides, comprising the steps of cyclizing a substituted alkynyl amide using a mild aqueous base in the presence of an organic solvent and a phase transfer agent to form a 5-methyleneoxazoline in a first step, chlorinating the 5-methyleneoxazoline in a solvent using trichloroisocyanuric acid to produce a chlorinated oxazoline intermediate in a second step, and subsequently hydrolyzing the chlorinated oxazoline intermediate with an aqueous acid to produce the desired monochloroketone in a third step. The ketone is typically isolated by a crystallization-filtration procedure.

Specifically, this embodiment provides a process for the preparation of an α-chloroketone compound of formula (I) comprising the steps of (i) cyclizing an alkynyl amide of formula (II) using a mild aqueous base in the presence of an organic solvent and a phase transfer agent (PTA) to form a 5-methyleneoxazoline of formula (III)

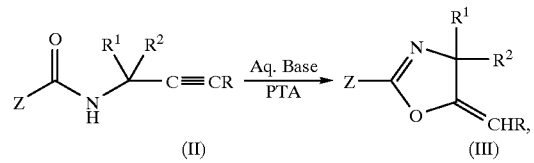

(ii) chlorinating the 5-methyleneoxazoline of formula (III) in a solvent using trichloroisocyanuric acid to produce a chlorinated oxazoline intermediate of formula (IV)

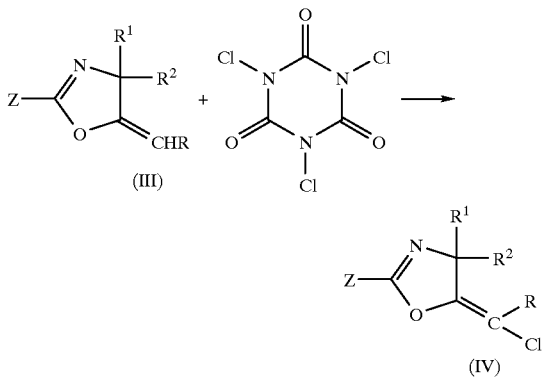

and (iii) hydrolyzing the chlorinated oxazoline intermediate of formula (IV) with an aqueous acid to produce the desired monochloroketone of formula (I)

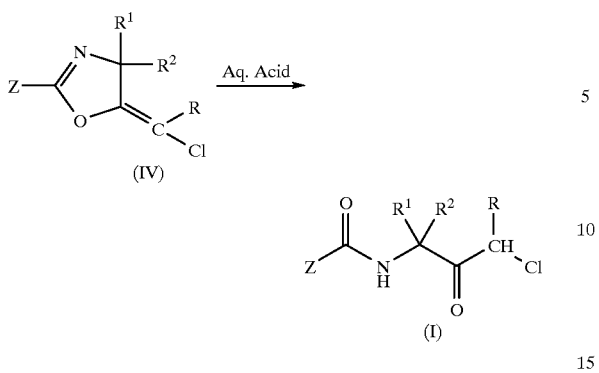

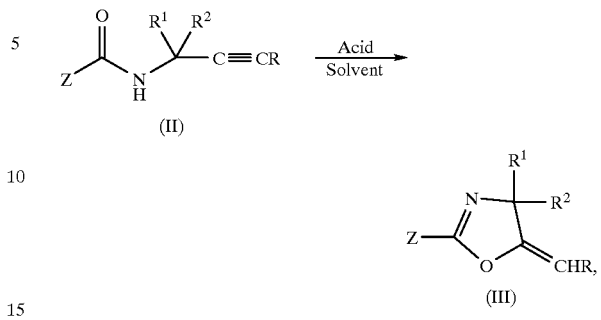

wherein
Z is alkyl or substituted alkyl, aryl or substituted aryl, heteroaryl or substituted heteroaryl or phenylene,
R is a hydrogen atom or alkyl, and
$R^1$ and $R^2$ are each independently an alkyl or substituted alkyl group, or $R^1$ and $R^2$ together with the carbon atom to which they are attached form a cyclic structure.

In a preferred form of this embodiment,
Z is $(C_1-C_8)$alkyl, phenyl or phenyl substituted with up to three substituents independently selected from the group consisting of halo, $(C_1-C_4)$alkyl, $(C_1-C_4)$alkoxy, $(C2-C_6)$alkynyl, nitro and cyano, 2-naphthyl, 3-pyridyl and 1,4-phenylene,
R is a hydrogen atom or a $(C_1-C_4)$alkyl, and
$R^1$ and $R^2$ are each independently a $(C_1-C_4)$alkyl or $R^1$ and $R^2$ together with the carbon atom to which they are attached form a cyclopentyl or cyclohexyl ring.

In a more preferred form of this embodiment,
Z is 3-heptyl, phenyl, 4-halophenyl, 2,6-dihalophenyl, 4-$(C_1-C_4)$alkylphenvl, 3,5-dilhalophenyl, 3,5-di$(C_1-C_4)$alkylphenyl, 4-$(C_1-C_4)$alkyl-3,5-dihalophenyl, 4-cyano-3,5-dihalophenyl, 4-$(C_1-C_4)$alkoxy-3,5-dihalophenyl, 4-nitrophenyl, 2-naphthyl, 3-pyridyl or 1,4-phenylene,
R is a hydrogen atom, methyl or ethyl, and
$R^1$ and $R^2$ are each independently methyl or ethyl or $R^1$ and $R^2$ together with the carbon atom to which they are attached form a cyclohexyl ring.

In an even more preferred form of this embodiment,
Z is 4-chlorophenyl, 2,6-difluorophenyl, 3,5-dimethylphenyl, 3,5-dichloro-4-methylphenyl, 4-nitrophenyl, 1,4-phenylene, 2-naphthyl, 3-pyridyl or 3-heptyl,
R is a hydrogen atom, and
$R^1$ and $R^2$ are each independently methyl or ethyl.

A second embodiment of this invention provides a convenient process to α-chloroketones, which are useful as fungicides, comprising the steps of cyclizing an alkynyl amide using an acid in the presence of an organic solvent under anhydrous conditions to form a 5-methyleneoxazoline in a first step, chlorinating the 5-methyleneoxazoline in a solvent using trichloroisocyanuric acid to produce a chlorinated oxazoline intermediate in a second step, and subsequently hydrolyzing the chlorinated oxazoline intermediate with an aqueous acid to produce the desired monochloroketone in a third step. The ketone is typically isolated by a crystallization-filtration procedure.

Specifically, this embodiment provides a process for the preparation of an α-chloroketone compound of formula (I) comprising the steps of (i) cyclizing an alkynyl amide of formula (II) using an acid to form a 5-methyleneoxazoline of formula (III)

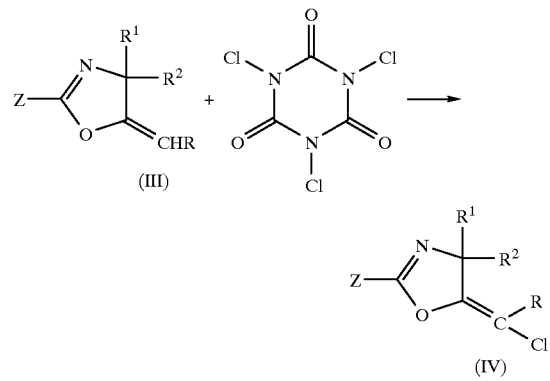

(ii) chlorinating the 5-methyleneoxazoline of formula (III) in a solvent using trichloroisocyanuric acid to produce a chlorinated oxazoline intermediate of formula (IV)

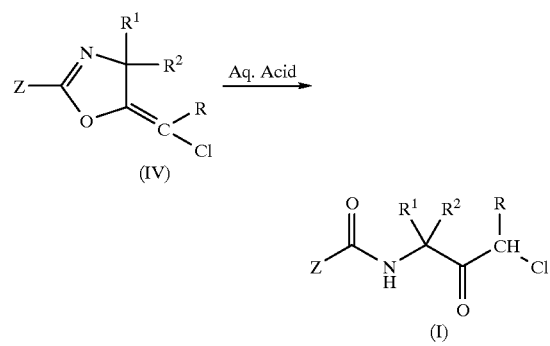

and
(iii) hydrolyzing the chlorinated oxazoline intermediate of formula (IV) with an aqueous acid to produce the desired monochloroketone of formula (I)

wherein
Z is alkyl or substituted alkyl, aryl or substituted aryl, heteroaryl or substituted heteroaryl or phenylene,
R is a hydrogen atom or alkyl, and
$R^1$ and $R^2$ are each independently an alkyl or substituted alkyl group, or $R^1$ and $R^2$ together with the carbon atom to which they are attached form a cyclic structure.

In a preferred form of this embodiment,
Z is $(C_1-C_8)$alkyl, phenyl or phenyl substituted with up to three substituents independently selected from the group consisting of halo, $(C_1-C_4)$alkyl, $(C_1-C_4)$alkoxy, $(C_2-C_6)$alkynyl, nitro and cyano, 2-naphthyl, 3-pyridyl and 1,4-phenylene, R is a hydrogen atom or a $(C_1-C_4)$alkyl, and $R^1$ and $R^2$ are each independently a $(C_1-C_4)$alkyl or $R^1$ and $R^2$ together with the carbon atom to which they are attached form a cyclopentyl or cyclohexyl ring.

In a more preferred form of this embodiment,

Z is 3-heptyl, phenyl, 4-halophenyl, 2,6-dihalophenyl, 4-$(C_1-C_4)$alkylphenyl, 3,5-dihalophenyl, 3,5-di$(C_1-C_4)$alkylphenyl, 4-$(C_1-C_4)$alkyl-3,5-dihalophenyl, 4-cyano-3,5-dihalophenyl, 4-$(C_1-C_4)$alkoxy-3,5-dihalophenyl, 4-nitrophenyl, 2-naphthyl, 3-pyridyl or 1,4-phenylene, R is a hydrogen atom, methyl or ethyl, and $R^1$ and $R^2$ are each independently methyl or ethyl or $R^1$ and $R^2$ together with the carbon atom to which they are attached form a cyclohexyl ring.

In an even more preferred form of this embodiment,

Z is 4-chlorophenyl, 2,6-difluorophenyl, 3,5-dimethylphenyl, 3,5-dichloro-4-methylphenyl, 4-nitrophenyl, 1,4-phenylene, 2-naphthyl, 3-pyridyl or 3-heptyl, R is a hydrogen atom, and $R^1$ and $R^2$ are each independently methyl or ethyl.

In both embodiments of this invention, the amount of TCIA which is employed in step (ii) may be advantageously increased in order to form 5-(dichloromethylene)oxazolines which are subsequently hydrolyzed to α,α-dichloroketones which are useful as fungicides. Specifically, this feature of this invention provides a process for the preparation of an α,α-dichloroketone compound of formula (IA) comprising the steps of (i) cyclizing an alkynyl amide of formula (IIA) to form a 5-methyleneoxazoline of formula (IIIA)

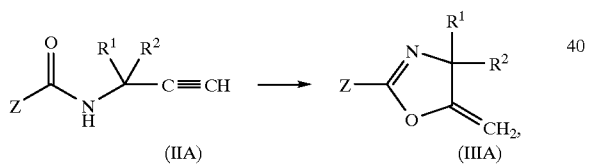

(ii) chlorinating the 5-methyleneoxazoline of formula (IIIA) in a solvent using trichloroisocyanuric acid to produce a dichlorinated oxazoline intermediate of formula (IVA)

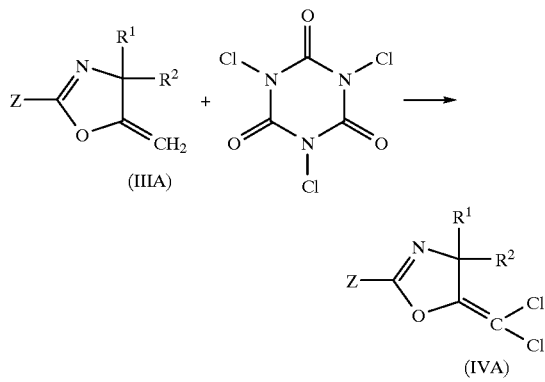

and (iii) hydrolyzing the dichlorinated oxazoline intermediate of formula (IVA) with an aqueous acid to produce the desired dichloroketone of formula (IA)

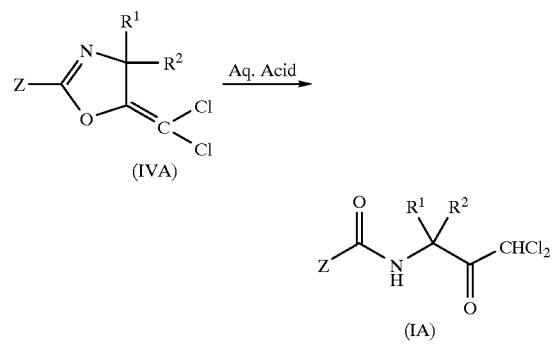

wherein

Z is alkyl or substituted alkyl, aryl or substituted aryl, heteroaryl or substituted heteroaryl or phenylene, and $R^1$ and $R^2$ are each independently an alkyl or substituted alkyl group, or $R^1$ and $R^2$ together with the carbon atom to which they are attached form a cyclic structure.

In a preferred form of this feature,

Z is $(C_1-C_8)$alkyl, phenyl or phenyl substituted with up to three substituents independently selected from the group consisting of halo, $(C_1-C_4)$alkyl, $(C_1-C_4)$alkoxy, $(C_2-C_6)$alkynyl, nitro and cyano, 2-naphthyl, 3-pyridyl and 1,4-phenylene, and $R^1$ and $R^2$ are each independently a $(C_1-C_4)$alkyl or $R^1$ and $R^2$ together with the carbon atom to which they are attached form a cyclopentyl or cyclohexyl ring.

In a more preferred form of this feature,

Z is 3-heptyl, phenyl, 4-halophenyl, 2,6-dihalophenyl, 4-$(C_1-C_4)$alkylphenyl, 3,5-dihalophenyl, 3,5-di$(C_1-C_4)$alkylphenyl, 4-$(C_1-C_4)$alkyl-3,5-dihalophenyl, 4-cyano-3,5-dihalophenyl, 4-$(C_1-C_4)$alkoxy-3,5-dihalophenyl, 4-nitrophenyl, 2-naphthyl, 3-pyridyl or 1,4-phenylene, and $R^1$ and $R^2$ are each independently methyl or ethyl or $R^1$ and $R^2$ together with the carbon atom to which they are attached form a cyclohexyl ring.

In an even more preferred form of this feature,

Z is 4-chlorophenyl, 2,6-difluorophenyl, 3,5-dimethylphenyl, 3,5-dichloro-4-methylphenyl, 4-nitrophenyl, 1,4-phenylene, 2-naphthyl, 3-pyridyl or 3-heptyl, and $R^1$ and $R^2$ are each independently methyl or ethyl.

In this invention, alkyl means a $(C_1-C_8)$ straight or a $(C_3-C_8)$ branched chain alkyl group and includes, for example, methyl, ethyl, 1i-propyl, isopropyl, n-butyl, isobutyl, sec-butyl, tert-butyl, n-amyl, isoamyl, n-hexyl, isooctyl and the like. Substituted alkyl means an alkyl substituted with one or more substituents selected from the group consisting of alkoxy, halo, alkylthio and cyano.

Alkoxy means a $(C_1-C_4)$ straight or a $(C_3-C_4)$ branched chain alkyl group attached to an oxygen atom, for example, methoxy, ethoxy, isobutoxy and the like.

Alkylthio means a $(C_1-C_4)$ straight or a $(C_3-C_4)$ branched chain alkyl group attached to an sulfur atom, for example, methylthio, n-propylthio, sec-butylthio and the like.

Halo means bromo, chloro, fluoro and iodo.

Aryl means phenyl, naphthyl, or phenyl or naphthyl substituted with one to three substituents independently selected from the group consisting of halo, alkyl, alkynyl, alkoxy, nitro or cyano. Examples include, but are not limited to, phenyl, 2-naphthyl, 4-nitrophenyl, 4-chlorophenyl, 3,5-dimethylphenyl, 2,6-ditluorophenyl, 3,5-dichloro-4-methylphenyl, 3,5-dichilorophenyl, 3,5-difluorophenyl, 3,5-dibromophenyl, 3-chloro-4-ethyl-5-fluorophenyl, 3,5-dichloro-4-cyanophenyl, 3,5-dichloro-4-methoxyplhenyl, 3,5-difluoro-4-propargyl phenyl, 3,5-dibromo-4-methylphenyl and the like.

Alkynyl means a $(C_2-C_6)$alkynyl, for example, ethynyl, propargyl, 2-hexynyl and the like.

Heteroaryl means a 5-membered aromatic ring which may contain an oxygen atom, a sulfur atom, 1, 2 or 3 nitrogen atoms, an oxygen atom with 1 or 2 nitrogen atoms or a sulfur atom with 1 or 2 nitrogen atoms, or a 6-membered aromatic ring containing 1, 2 or 3 nitrogen atoms, or heteroaryl substituted with up to two substituents selected from halo, alkyl, haloalkyl or cyano. Examples include, but are not limited to 2-furyl, 2-thienyl, 4-chloro-2-thienyl, 2-oxazolyl, 2-imidazolyl, 1,2,4-triazol-1-yl, 2-imidazolyl, 2-pyrrolyl, 2-pyridyl, 3-pyridyl, 4-pyridyl, 4-pyridazinyl, 4-pyrimidinyl, 2-pyrazinyl, 1,3,5-triazin-2-yl, 4-chloro-3-pyridyl and the like.

Phenylene means 1,4-phenylene.

Although a specific isomer is shown throughout for the compound of formula (IV), it is to be understood that formula (IV) actually represents a mixture of the cis and trans isomeric forms.

In the first embodiment of this invention, the cyclization step (i) to form a 5-methyleneoxazoline from an alkynyl amide is carried out using a mild aqueous base in the presence of a phase transfer agent. Although the phase transfer agent (PTA) is required, the choice of PTA which is employed is not critical and may be non-ionic, cationic or amphoteric in nature. Examples of the PTA include, but are not limited to, an alkylphenoxy polyethoxy ethanol, a quaternary ammonium halide such as tetrabutylammonium bromide, benzyltributylammonium chloride or tricaprylylmethylammonium chloride which is sold under the tradename of Aliquat® 336, and a quaternary phosphonium halide such as a $(C_{16}-C_{18})$alkyltribtitylphosphonium bromide such as cetyltributylphosphonium bromide. The amount of PTA employed is also not overly critical, but is generally in the range of from about 0.1% to about 25% by weight, preferably from about 0.1% to about 10% by weight, based on the alkynyl amide starting material. The reaction temperature is usually from about 25° C. up to the boiling point of the solvent/water system used. A preferred condition is a reaction temperature of at least 50° C. up to the boiling point of the solvent/water system used. Pressure is not important, but the reaction is usually run at atmospheric pressure for convenience. The time of the reaction will depend upon the temperature employed, the substituent pattern of the starting alkynyl amide, the solvent utilized, the nature of the base and the PTA, and the size and design of the reactor. However, the reaction is usually conveniently effected in a time of 24 hours or less and more usually 10 hours or less.

Most common aqueous bases can be used for the formation of the oxazoline from the alkynyl amide. A basic ion exchange resin may also be used. Preferred bases are sodium hydroxide (NaOH) and potassium hydroxide (KOH) or mixtures thereof, sodium carbonate ($Na_2CO_3$) and potassium carbonate ($K_2CO_3$) or mixtures thereof, and sodium bicarbonate ($NaHCO_3$) and potassium bicarbonate ($KHCO_3$) or mixtures thereof. More preferred are NaOH, KOH, $NaHCO_3$ and $Na_2CO_3$. Even more preferred is NaOH. Various solvents can be used in this reaction. They can be either non-polar, for example an aliphatic hydrocarbon such as heptane and isooctane or an aromatic hydrocarbon such as toluene and a xylene, or polar, for example an ether. Generally, the hydroxide type bases are best used in a non-polar solvent in order to avoid side reactions. The bicarbonate and carbonate type bases can be used with either type solvent, but are usually advantageously employed with the polar types. The amount of base employed is usually at least 0.05 equivalent per equivalent of alkynyl amide. A preferred amount is at least 0.1 equivalent of base. A more preferred amount is at least 0.25 equivalent of base.

In a typical representative reaction procedure for this first embodiment for step (i), the alkynyl amide, solvent, base and phase transfer agent are added together and heated at reflux until no starting material could be detected by gas chromatographic (GC) analysis. After cooling, the lower aqueous layer is discarded and the organic solution is washed with brine, dried over a desiccant, and filtered. If desired, the filtrate can be further treated with decolorizing charcoal and refiltered. The solution is concentrated to remove most of the solvent and the resulting clear oil distilled under vacuum to afford the 5-methyleneoxazoline material.

In the second embodiment of this invention, the cyclization step (i) to form a 5-methyleneoxazoline from an alkynyl amide is carried out using an acid, preferably an anhydrous acid, in the presence of an organic solvent. The acid may be either a mineral or an organic acid. Examples of the acid include, but are not limited to, oleum, methanesulfonic acid, toluenesulfonic acid, trifluoroacetic acid and trichloroacetic acid. Preferred acids are methanesulfonic acid and trichloroacetic acid. A more preferred acid is methanesulfonic acid. The amount of acid employed can vary, but an amount of from about 5 mole percent to about 200 mole percent, based on the starting substituted amide material, is generally used. A preferred amount is from about 5 mole percent to about 100 mole percent. A more preferred amount is from about 5 mole percent to about 20 mole percent. The solvent employed can be either a polar or non-polar solvent and is preferably anhydrous in nature. Examples of polar solvents include, but are not limited to, esters such as ethyl acetate and butyl acetate, ethers such as methyl tert-butyl ether, and nitriles such as acetonitrile. Examples of non-polar solvents include, but are not limited to, aliphatic hydrocarbons such as heptane, aromatic hydrocarbons such as toluene, and haloaromatic hydrocarbons such as chlorobenzene. Preferred solvents are butyl acetate, chlorobenzene and heptane. The reaction temperature is usually from about 20° C. to the reflux temperature of the solvent system employed. A preferred temperature is from about 25° C. to about 130° C. A more preferred temperature is from about 80° C. to about 120° C. Pressure is not important, but the reaction is usually run at atmospheric pressure for convenience. The time of the reaction will depend upon the temperature employed, the substituent pattern of the starting alkynyl amide, the solvent utilized, the nature of the acid, and the size and design of the reactor. However, the reaction is usually conveniently effected in a time of from about 2 hours to about 5 days and more usually 3 days or less.

In a typical representative reaction procedure for step (i) of this second embodiment, the starting amide is added to the reaction solvent followed by the catalyst. The reaction is then brought to temperature and stirrred until complete, cooled to ambient temperature and quenched with saturated sodium bicarbonate. The layers are separated, aqueous extracted, organics combined, dried, filtered and evaporated to dryness to give the desired product.

In both the embodiments of this invention, the chlorination step (ii) of the 5-methyleneoxazoline using TCIA may be performed at a temperature of from about −30° to about 100° C. A preferred chlorination temperature is from about 0° to 70° C. More preferred in order to obtain the best chlorination selectivity is a temperature of about 50° C. or lower. Even more preferred is a temperature from 0° to 30° C. The reaction is not pressure-dependent, but a pressure of 1 atmosphere is usually preferred for convenience. The stoichiometry of the reagents is extremely important. If less than 0.333 equivalent of TCIA per equivalent of 5-methyleneoxazoline is used, some of the 5-methyleneoxazoline starting material will remain unreacted. If greater than 0.333 equivalent is used, an overchlorinated intermediate is formed that leads to a dichloroketone after hydrolysis. However, as noted previously, an added feature of this invention provides for the convenient formation of a 5-(dichloromethylene)oxazoline and subsequent formation in step (iii) of an α,α-dichloroketone when ≧0.667 equivalent of TCIA is used per equivalent of the 5-methyleneoxazoline in the situation where the methylene group of the oxazoline is not substituted with an alkyl group. The chlorination reaction time can vary from about 5 minutes to about 1 hour and is dependent on both the size and type of reactor equipment employed and the solvent used. The chlorination solvent is usually a polar solvent such as, but not limited to, an ether, an ester or a ketone, for example ethyl acetate, butyl acetate and methyl t-butyl ether. Preferred solvents are ethyl acetate or butyl acetate. Nonpolar solvents such as an aromatic hydrocarbon, for example toluene, or an aliphatic hydrocarbon, for example heptane and isooctane, may be also employed when admixed with a miscible polar type solvent or when heated to a temperature of about 40° C. After the chlorination reaction is carried out to the desired stage, the cyanuric acid by-product may be removed by filtration and/or by washing with a common base such as sodium carbonate, sodium hydroxide and the like. The resulting solution containing the 5-chloromethyleneoxazoline is then subjected to the hydrolysis step (iii).

In the hydrolysis step (iii), a temperature of about 50° C. or higher is required. Preferably, the hydrolysis is performed from about 50° to 100° C. More preferably, the temperature employed is from about 50° to 80° C. Either an aqueous acid or a non-aqueous acid admixed with some water may be employed. A common acid such as, but nt)t limited to, hydrochloric acid, sulfuric acid, trifluoroacetic acid, methanesulfonic acid or toluenesulfonic acid is convenient to use. Aqueous hydrochloric acid or sulfuric acid are preferred An acidic ion-exchange resin may also be utilized. When hydrochloric acid or sulfuric acid are used, additional water is usually added to facilitate the hydrolysis. It is preferred that about 0.05 to 0.5 equivalent of an aqueous acid is used per equivalent of 5-chloromethyleneoxazoline. More preferred is the use of about 0.1 to 0.25 equivalent of aqueous hydrochloric acid per equivalent of 5-chloromethyleneoxazoline. The hydrolysis step usually takes from about 3 to about 24 hours, with the time depending on the nature of the Z group, the temperature and the size and nature of the equipment employed. The pressure used is not critical. However, 1 atmosphere is usually preferred for convenience.

In a typical representative reaction procedure for steps (ii) and (iii) of both embodiments, the oxazoline and solvent are combined and the resulting solution is chilled to 0–5° C. using an ice bath. The TCIA is added gradually, keeping the reaction temperature below 30° C. if possible. Once the TCIA has been added, the resulting slurry is warmed to room temperature and stirred until the reaction is complete based on gas chromatographic (GC) analysis. The cyanuric acid by-product is removed by filtration and the solution is then washed with an appropriate base such as a sodium bicarbonate or sodium hydroxide solution to remove any remaining cyanuric acid. The solution containing the 5-chloromethyleneoxazoline is returned to the flask and heated to 60° C. Concentrated hydrochloric acid and water are added and the solution is stirred until the hydrolysis is complete The reaction mixture is cooled to room temperature and the desired α-chloroketone crystallizes on cooling. The solid obtained is filtered, washed and dried to give the product. A second crop is frequently obtained by concentration and cooling of the filtrate solution.

The following examples, tables and experimental procedures are provided for guidance to the practitioner and are not meant to limit the scope of the invention which is defined by the claims.

TABLE I

EXAMPLES B1 to B14
Base Catalyzed Formation of 5-Methyleneoxazolines from
Alkynyl Amides in the Presence of a Phase Transfer Agent (PTA)

$$\underset{H}{\overset{O}{\underset{N}{\parallel}}}{Z-C-N}\overset{R^1\ R^2}{\underset{}{-C-}}C\equiv CH \xrightarrow{\text{Aq. Base} \atop \text{PTA}}$$

$$Z-\underset{O}{\overset{N}{\parallel}}\overset{R^1}{\underset{CH_2}{\rightthreetimes R^2}}$$

| Example No. B | Z | $R^1$ | $R^2$ | Yield (%) | bp °C. (mm Hg) |
|---|---|---|---|---|---|
| 1, 2, 3 | phenyl | $CH_3$ | $CH_3$ | 95, 98, 92 | 70–75 (0.6) |
| 4, 5 | 3,5-dimethylphenyl | $CH_3$ | $CH_3$ | 98, 98 | 86–94 (0.4) |
| 6 | 4-chlorophenyl | $CH_3$ | $C_2H_5$ | 97 | 95 (0.6) |
| 7 | 2,6-difluorophenyl | $CH_3$ | $CH_3$ | 95 | 80 (1.0) |
| 8 | 2,6-difluorophenyl | —$(CH_2)_5$— | | 96 | 110–112 (0.5) |
| 9 | 3,5-dichloro-4-methylphenyl | $CH_3$ | $C_2H_5$ | 87 | 128 (1.0) |
| 10 | 4-nitrophenyl | $CH_3$ | $CH_3$ | 90 | mp 91–94 |
| 11 | 1,4-phenylene | $C_2H_5$ | $C_2H_5$ | 87 | mp 143–144 |
| 12 | 2-naphthyl | $CH_3$ | $CH_3$ | 95 | 132–137 (0.5) |
| 13 | 3-pyridyl | $CH_3$ | $CH_3$ | 96 | 80–87 (0.6) |
| 14 | heptan-3-yl | $CH_3$ | $CH_3$ | 98 | 62 (1.0) |

EXAMPLE B1

Preparation of 4,4-dimethyl-5-methylene-2-phenyloxazoline

To a round bottom flask equipped with a magnetic stir bar, heating mantle, and reflux condenser was added N-(3-methylbutyn-3-yl)benzamide (25.00 g, 133.5 mmol), 200 mL of toluene, 27 mL of 0.5 N aqueous sodium hydlroxide, and 2.00 g (4.95 mmol, 3.7 mol %) of Aliquat® 336. The resulting mixture was heated at reflux for 3 h at which time no starting material could be detected by gas chromatographic (GC) analysis. After cooling, the mixture was transferred to a separatory funnel. The lower aqueous layer was discarded. The organic solution was washed with brine, dried over MgSO$_4$, and filtered. The filtrate was treated with 2.0 g of decolorizing charcoal and filtered again. The solution was concentrated using a rotary evaporator to afford 26.41 g of a clear oil. The product was distilled under 70–75° C., 0.6 mm Hg) to afford 23.65 (95% yield) of a clear colorless liquid. This material, 4,4-dimethyl-5-methylene-2-phenyloxazoline, was found to be a single component by gas chromatographic analysis: $^1$H NMR (400 MHz, CDCl$_3$) δ 7.99 (d, J=6.7 Hz, 2H), 7.50–7.35 (m, 3H), 4.73 (d, J=2.8 Hz, 1H), 4.23 (d, J=2.8 Hz, 1H), 1.45 (s, 6H); $^{13}$C NMR (100 MHz, CDCl$_3$) δ 167.8, 159.8, 131.6, 128.4, 126.0, 126.95, 82.3, 69.0, 29.7.

EXAMPLE B2

Preparation of 4,4-dimethyl-5-methylene-2-phenyloxazoline

In a manner similar to example 1, a 98% yield of 4,4-dimethyl-5-methylene-2-phenyloxazoline was obtained using methyl tert-butyl ether in place of toluene, and a reaction time of 4 h.

EXAMPLE B3

Preparation of 4,4-dimethyl-5-methylene-2-phenyloxazoline

In a manner similar to example 1, a 92% yield of 4,4-dimethyl-5-methylene-2-phenyloxazoline was obtained using chlorobenzene in place of toluene, and a reaction time of 2.5 h.

EXAMPLE B4

Preparation of 2-(3,5-dimethylphenyl)-4,4-dimethyl-5-methyleneoxazoline

To a round bottom flask equipped with a magnetic stir bar, heating mantle, and reflux condenser was added N-(3-methylbutyn-3-yl)-3,5-dimethylbenzamide (25.00 g, 116.1 mmol), 200 mL of toluene, 50 mL of 0.5 N aqueous sodium hydroxide, and 1.74 g (4.31 mmol, 3.7 mol %) of Aliquat® 336. The resulting mixture was heated at reflux for 1.5 h. After cooling, the mixture was transferred to a separatory funnel. The lower aqueous layer was discarded. The organic solution was washed with brine, dried over MgSO$_4$, and filtered. The solution was concentrated using a rotary evaporator to afford a clear colorless oil which was distilled (86–94° C., 0.4 mm) to give 24.43 g (98%) of 2-(3,5-dimethylphenyl)-4,4-dimethyl-5-methyleneoxazoline as a colorless liquid: $^1$H NMR (400 MHz, CDCl$_3$) δ 7.62 (s, 2H), 7.09 (s, 1H), 4.73 (d, J=3.2 Hz, 1H), 4.22 (d, J=3.2 Hz, 1H), 2.30 (s, 6H), 1.44 (s, 6H); $^{13}$C NMR (100 MHz, CDCl$_3$) δ 167.9, 160.1, 138.1, 133.3, 126.7, 125.8, 82.1, 68.9, 29.8, 2.1.

EXAMPLE B5

Preparation of 2-(3,5-dimethylphenyl)-4,4-dimethyl-5-methyleneoxazoline

In a manner similar to example 4, a 98% yield of 2-(3,5-dimethylphenyl)-4,4-dimethyl-5-methyleneoxazoline was obtained using isooctane as the solvent, 2.95 g of hexadecyltributylphosphonium bromide as the phase transfer catalyst, and a reaction time of 2 h.

EXAMPLE B6

Preparation of 2-(4-chlorophenyl)-4-ethyl-4-methyl-5-methyleneoxazoline

In a manner similar to example 4, a 97% yield of 2-(4-chlorophenyl)-4-ethyl-4-methyl-5-methyleneoxazoline was obtained using isooctane as the solvent, 2.84 g of octadecyltributylphosphonium bromide as the phase transfer catalyst, and a reaction time of 1.5 h: bp (95° C., 0.6 mm); mp 55–57° C.; $^1$H NMR (400 MHz, CDCl$_3$) δ 7.92 (d, J=8.8 Hz, 2H), 7.38 (d, J=8.8 Hz, 2H), 4.80 (d, J=2.4 Hz, 1H), 4.19 (d, J=2.4 Hz, 1H), 1.86 (dt, J=20.8, 7.5 Hz, 1H), 1.60 (dt, J=20.8, 7.5 Hz, 1H), 1.42 (s, 3H), 0.80 (t, J=7.5 Hz, 3H); $^{13}$C NMR (100 MHz, CDCl$_3$) δ 166.0, 159.0, 137.8, 129.4, 128.7, 125.4, 83.1, 72.9, 35.0, 28.6, 8.3.

EXAMPLE B7

Preparation of 2-(2,6-difluorophenyl)-4,4-dimethyl-5-methyleneoxazoline

In a manner similar to example 4, a 95% yield of 2-(2,6-difluorophenyl)-4,4-dimethyl-5-methyleneoxazoline was obtained using isooctane as the solvent, 2.26 g of Aliquat® 336 as the phase transfer catalyst, and a reaction time of 1.25 h: bp (80° C., 1.0 mm); $^1$H NMR (400 MHz, CDCl$_3$) δ 7.42 (tt, J=8.0, 6.0 Hz, 1H), 6.98 (t, J=8.0 Hz, 2H), 4.74 (d, J=3.2 Hz, 1H), 4.30 (d, J=3.2 Hz, 1H), 1.45 (s, 6H); $^{13}$C NMR (100 MHz, CDCl$_3$) δ 167.1, 161.2 (dd, J=256.7, 5.7 Hz), 152.6, 132.8 (t, J=10.3 Hz), 112.0 (d, J=20.0 Hz), 106.7 (t, J=17.1 Hz), 83.0, 69.4, 29.6.

EXAMPLE B8

Preparation of 2-(2,6-difluorophenyl)-5-methylene-4,4-(pentamethylene)oxazoline

In a manner similar to example 4, a 96% yield of 2-(2,6-difluorophenyl)-5-methylene-4,4-(pentamethylene) oxazoline was obtained using toluene as the solvent, 2.41 g of hexadecyltributylphosphonium bromide as the phase transfer catalyst, and a reaction time of 6 h: bp (110–112° C., 0.5 mm); mp 43–46° C.; $^1$H NMR (400 MHz, CDCl$_3$) δ 7.38 (tt, J=8.4, 6.0 Hz, 1H), 6.94 (t, J=8.8 Hz, 2H), 4.72 (d, J=3.2 Hz, 1H), 4.26 (d, J=3.2 Hz, 1H), 2.0–1.3 (m, 10H); $^{13}$C NMR (100 MHz, CDCl$_3$) δ 167.6, 161.2 (dd, J=256.3, 6.0 Hz), 151.9, 132.6 (t, J=10.3 Hz), 111.9 (dd, J=20.2, 5.4 Hz), 107.2 (t, J=18.3 Hz), 83.2, 72.6, 39.3, 25.6, 22.2.

EXAMPLE B9

Preparation of 2-(3,5-dichloro-4-methylphenyl)-4-ethyl-4-methyl-5-methyleneoxazoline In a manner similar to example 4, a 87% yield of 2-(3,5-dichloro-4-methylphenyl)-4-ethyl-4-methyl-5-methyleneoxazoline was obtained using heptane as the solvent, 1.08 g of Aliquat® 336 as the phase transfer catalyst, a solution of 10.2 g sodium carbonate in 80 mL water, and a reaction time of 1.5 h: bp (128° C., 1.0 mm); $^{13}$C NMR (100 MHz, DMSO-d$_6$) δ 165.1, 156.5, 137.6, 135.0, 126.5, 126.0, 83.9, 72.7, 34.0, 28.0, 17.4, 8.1.

EXAMPLE B10

Preparation of 2-(4-nitrophenyl)-4,4-dimethyl-5-methyleneoxazoline

In a manner similar to example 4, a 90% yield of 2-(4-nitrophenyl)-4,4-dimethyl-5-methyleneoxazoline was obtained using isooctane as the solvent, 2.25 g of Aliquat® 336 as the phase transfer catalyst, and a reaction time of 1.25 h. The crude product was recrystallized from hexane to give 22.61 g of a light orange solid: mp 91–94° C.; $^1$H NMR (400 MHz, CDCl$_3$) δ 8.29 (d, J=8.8 Hz, 2H), 8.16 (d, J=8.8 Hz, 2H), 4.80 (d, J=3.2 Hz, 1H), 4.33 (d, J=3.2 Hz, 1H), 1.48 (s, 6H); $^{13}$C NMR (100 MHz, CDCl$_3$) δ 167.3, 158.1, 149.6, 132.8, 129.1, 123.6, 83.5, 69.7, 29.6.

EXAMPLE B11

Preparation of bis(4,4-diethyl-5-methyleneoxazolin-2-yl)-1,4-phenylene

In a manner similar to example 4, a 87% yield of bis(4,4-diethyl-5-methyleneoxazolin-2-yl)-1,4-phenylene was obtained using toluene as the solvent, 2.00 g of Aliquat® 336 as the phase transfer catalyst, 50 mL of 1 N NaOH solution, and a reaction time of 2 h. The crude product was recrystallized from hexane to give 21.81 g of a white solid: mp 143–144° C.; $^1$H NMR (400 MHz, CDCl$_3$) δ 8.09 (s, 4H), 4.90 (d, J=3.2 Hz, 2H), 4.17 (d, J=3.2 Hz, 2H), 1.92 (dt, J=21.2, 7.4 Hz, 4H), 1.58 (dt, J=21.2, 7.4 Hz, 4H), 8.81 (t, J=7.4Hz, 12H); $^{13}$C NMR (100 MHz, CDCl$_3$) δ 164.0, 159.5, 129.6, 128.2, 83.6, 77.2, 34.0, 8.1.

EXAMPLE B12

Preparation of 4,4-dimethyl-5-methylene-2-(2-naphthyl)oxazoline

In a manner similar to example 4, a 95% yield of 4,4-dimethyl-5-methylene-2-(2-naphthyl)oxazoline was obtained using toluene as the solvent, 1.00 g of Aliquat® 336 as the phase transfer catalyst, 50 mL of 1 N NaOH solution, and a reaction time of 1.5 h: bp (132–137° C., 0.5 mm); $^1$H NMR (400 MHz, CDCl$_3$) δ 8.46 (s, 1H), 8.04 (dd, J =8.8, 2.0 Hz, 1H), 7.84 (dd, J=6.4, 2.4 Hz, 1H), 7.79 (d, J=8.4 Hz, 1H), 7.75 (dd, J=6.8, 2.8 Hz, 1H), 7.48–7.40 (m, 2H), 4.78 (d, J=2.8 Hz, 1H), 4.25 (d, J=2.8 Hz, 1H), 1.48 (s, 6H); $^{13}$C NMR (100 MHz, CDCl$_3$) δ 167.8, 159.9, 134.7, 132.6, 128.8, 128.7, 128.2, 127.7, 127.6, 126.5, 124.3, 124.1, 82.3, 69.1, 29.8.

EXAMPLE B13

Preparation of 4,4-dimethyl-5-methylene-2-(3-pyridyl)oxazoline

In a manner similar to example 4, a 96% yield of 4,4-dimethyl-5-methylene-2-(3-pyridyl)oxazoline was obtained using isooctane as the solvent, 2.00 g of stearyltributylphosphonium bromide as the phase transfer catalyst, 50 mL of 0.5 N NaOH solution, and a reaction time of 1 h: bp 80–87° C. (0.6 mm); $^{13}$C NMR (100 MHz, CDCl$_3$) δ 164.9, 152.0, 148.0, 135.2, 123.4, 86.8, 69.7, 48.2, 29.0.

EXAMPLE B14

Preparation of 2-heptan-3-yl-4,4-dimethyl-5-methyleneoxazoline

In a manner similar to example 4, a 98% yield of 2-heptan-3-yl-4,4-dimethyl-5-ethyleneoxazoline was obtained using heptane as the solvent, 4.81 g of Aliquat® 336 as the phase transfer catalyst, KOH instead of NaOH, and a reaction time of 2 h: bp (62° C., 1.0 mm); $^{13}$C NMR (100 MHz, CDCl$_3$) δ 168.2, 165.8, 81.4, 68.1, 41.0, 31.8, 29.8, 29.5, 25.4, 22.6, 14.0, 11.7.

COMPARATIVE EXAMPLES

Base Catalyzed Cyclization without the Presence of a PWA

To further demonstrate the utility of the present invention whereby the 5-methyleneoxazoline is formed from a substituted amide using a base in the presence of a PTA, the following comparative examples were performed without a PTA being present.

COMPARATIVE EXAMPLE B-1

When an experiment was run in a manner similar to example B4 but in the absence of any phase-transfer catalyst, only 21% of 2-(3,5-dimethylphenyl)-4,4-dimethyl-5-methyleneoxazoline was obtained using heptane as the solvent and a reaction time of 8 h. The other 79% of the recovered material consisted of unreacted N-(3-methylbutyn-3-yl)-3,5-dimethylbenzamide.

COMPARATIVE EXAMPLE B-2

When an experiment was run in a manner similar to example B4 using toluene as solvent but in the absence of any phase-transfer catalyst, N-(3-methylpentyn-3-yl)-3,5-dichloro-4-methylbenzamide was recovered unchanged after a reaction time of 8 h.

The following procedure for the acid catalyzed formation of the 5-methyleneoxazoline from a substituted amide was ut5ilized for all examples A1 to A18 shown in Table II:

To 2 g of aminoalkyne in 10 mL of solvent was added from 5 to 200 mol % of acid catalyst. The mixture was then heated to the desired temperature. Anhydrous starting materials are used. The reaction was stirred until GC analysis indicated starting material had been consumed or the reaction was no longer consuming starting material. It was then cooled to room temperature where it was quenched with 15 mL of saturated aqueous sodium bicarbonate solution and the layers separated. The aqueous layer was extracted with ethyl acetate (15 mL), the organics were combined, dried over sodium sulfate, filtered and evaporated to dryness in vacuo to give the desired product in the yield shown in Table II Products were identified by comparison to known standards and by $^1$H NMR spectroscopy.

TABLE II: EXAMPLES A1 TO A18 (following page)

Acid Catalyzed Formation of 5-Methyleneoxazolines from Alkynvl Amides

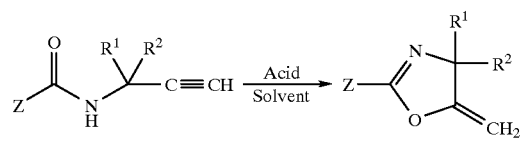

In Table II, weight yield refers to the aggregate of the desired 5-methyleneoxazoline product, a ketone having the formula

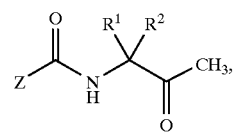

and the substituted amide starting material.

Examples C1–C11 illustrate the experimental conditions utilized in the preparation of the desired α-monochloroketones from the 5-methyleneoxazoline, prepared by either the base catalyzed cyclization in the presence of a PTA or the acid catalyzed cyclization of the substituted amide starting material, using TCIA and followed by hydrolysis using aqueous acid.

TABLE II

Acid Catalyzed Formation of 5-Methyleneoxazolines from Acetylenic Amides

| Example A | Z | $R^1$ | $R^2$ | Acid (amount in mol %) | Solvent | React. Time | Reaction Temperature | Weight Yield | % Product | % Ketone | % amide |
|---|---|---|---|---|---|---|---|---|---|---|---|
| 1 | 3,5-dichloro-4-methylphenyl | $CH_3$ | $C_2H_5$ | p-toluenesulfonic acid (5%) | ethyl acetate | 6 h | reflux | 90% by GC | 72 | 18.8 | 0 |
| 2 | 3,5-dichloro-4-methylphenyl | $CH_3$ | $C_2H_5$ | $CH_3CO_2H$ (150%) | butyl acetate | 3 d | reflux | 87% by GC | 71 | 0 | 16 |
| 3 | 3,5-dichloro-4-methylphenyl | $CH_3$ | $C_2H_5$ | $F_3CCO_2H$ (5%) | butyl acetate | 2 d | 20° C.-reflux | 92.4% by GC | 81 | 5 | 7 |
| 4 | 3,5-dichloro-4-methylphenyl | $CH_3$ | $C_2H_5$ | Oleum (5%) | butyl acetate | 6 h | 20–25° C. | 90.6% by GC | 70 | 6.6 | 14 |
| 5 | 3,5-dichloro-4-methylphenyl | $CH_3$ | $C_2H_5$ | $CH_3SO_3H$ (5%) | butyl acetate | 5 h | reflux | 93% by GC | 71 | 22 | 0 |
| 6 | 3,5-dichloro-4-methylphenyl | $CH_3$ | $C_2H_5$ | $CH_3SO_3H$ (5%) | butyl acetate[a] | 2 d | reflux | 80% by GC | 67 | 13 | 0 |
| 7 | 3,5-dichloro-4-methylphenyl | $CH_3$ | $C_2H_5$ | $CH_3SO_3H$ (5%) | butyl acetate[b] | 5 h | reflux | 92.8% by GC | 89 | 3.8 | 0 |
| 8 | 3,5-dichloro-4-methylphenyl | $CH_3$ | $C_2H_5$ | p-toluenesulfonic acid (5%) | butyl acetate/ acetic anhydride (2:1) | 2 d | reflux | 90.5% by GC | 87 | 3.5 | 0 |
| 9 | 4-nitrophenyl | $CH_3$ | $CH_3$ | $CH_3SO_3H$ (10%) | butyl acetate | 15–18 h | 80° C. | 92% isolated | 88 | 9.2 | 0 |
| 10 | 4-nitrophenyl | $CH_3$ | $CH_3$ | $CH_3SO_3H$ (5%) | heptane | 3 h | 90° C. | 95.6% isolated | 99.3 | 0.7 | 0 |
| 11 | 4-nitrophenyl | $CH_3$ | $CH_3$ | $CH_3SO_3H$ (5%) | acetonitrile | 2 d | reflux | 99.7% by GC | 81 | 17 | 1.7 |
| 12 | 4-nitrophenyl | $CH_3$ | $CH_3$ | $CH_3SO_3H$ (5%) | toluene | 3 h | reflux | 91.6% isolated | 98 | 2 | 0 |
| 13 | 4-nitrophenyl | $CH_3$ | $CH_3$ | $CH_3SO_3H$ (5%) | chlorobenzene | 2 h | 90° C. | 83% isolated | 100 | 0 | 0 |
| 14 | 4-nitrophenyl | $CH_3$ | $CH_3$ | $CH_3SO_3H$ (5%) | butyl acetate | 4 h | 90° C. | 99% isolated | 89 | 9 | 0 |
| 15 | 2-heptyl | $CH_3$ | $CH_3$ | $Cl_3CCO_2H$ (200%) | heptane | 4 h | reflux | 90% isolated | 100 | 0 | 0 |
| 16 | 2-heptyl | $CH_3$ | $CH_3$ | $CH_3SO_3H$ (5%) | heptane | 3 h | reflux | 93.5% isolated | 98.8 | 0 | 1 |
| 17 | 3,5-Dimethylphenyl | $CH_3$ | $CH_3$ | $CH_3SO_3H$ (5%) | heptane | 2 h | 85–90° C. | 94.8% isolated | 100 | 0 | 0 |
| 18 | 2,6-Difluorophenyl | $CH_3$ | $CH_3$ | $Cl_3CCO_2H$ (100%) | t-butyl methyl ether | 5 d | 50° C. | 97% isolated | 94.3 | 5.7 | 0 |

[a] 2 equivalents of butyl acetate added at the beginning of the reaction.
[b] 0.5 equivalent of acetic anhydride added at the beginning of the reaction.

EXAMPLE C1

Preparation of N-(1-chloro-3-methyl-2-oxobut-3-yl)-4-nitrobenzamide

A solution of 4,4-dimethyl-5-methylene-2-(4-nitrophenyl)oxazoline (10.0 g, 43.1 mmol) and ethyl acetate (35 mL) was cooled to 5° C. using an ice bath. Trichloroisocyanuric acid (3.33 g, 14.3 mmol) was added in several portions over 15 minutes in order to keep the reaction temperature below 40° C. When the addition was complete the reaction mixture was cooled to 20° C., and the ice bath was removed. The reaction was monitored by GC analysis for disappearance of the starting material. After 1.5 h, an additional 0.25 g (1.07 mmol) of the chlorinating agent was added in order to complete the chlorination. When the reaction was complete, the mixture was filtered. The filtrate was washed with ethyl acetate (15 mL). The filtrate was transferred to a round-bottom flask and heated to 60° C.; hydrochloric acid (0.85 g of a 37% solution) and water (2.8 mL) were added. The reaction mixture was stirred at 60° C. for 5 h, then cooled to room temperature. The resulting slurry was stored in a refrigerator overnight. The mixture was filtered, and the solids were rinsed with cold filtrate solution. The filtrate was concentrated to approximately half of its original volume by evaporation under reduced pressure. Hexane was gradually added until the solution clouded; the flask was chilled in a refrigerator at 8° C. overnight, then the slurry was filtered to obtain a second crop of crystals. Both crops were dried at 60° C. under vacuum, yielding N-(1-chloro-3-methyl-2-oxobut-3-yl)-4-nitrobenzamide (10.78 g, 88%) as a white solid, (mp 181–182° C.).

By following substantially the same procedure, the compounds of Examples C2–C11 were prepared as shown in Table III.

TABLE III

Preparation of α-Chloroketones from a
5-Methyleneoxazoline and TCIA, Followed by Hydrolysis

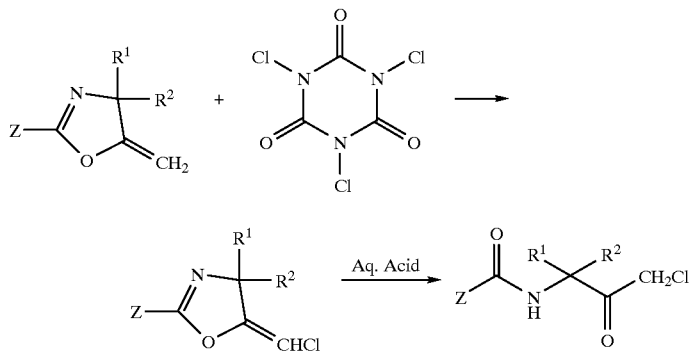

| Example No. C | Z | R¹ | R² | Product Yield (%) | mp (°C.) |
|---|---|---|---|---|---|
| 1 | 4-nitrophenyl | $CH_3$ | $CH_3$ | 88 | 181–182 |
| 2 | 4-chlorophenyl | $CH_2CH_3$ | $CH_3$ | 76 | 113–114 |
| 3 | 3,5-dimethylphenyl | $CH_3$ | $CH_3$ | 75 | 162–164 |
| 4 | 2,6-difluorophenyl | $CH_3$ | $CH_3$ | 75 | 191–192 |
| 5 | 2,6-difluorophenyl | —$(CH_2)_5$— | | 74 | 171–172 |
| 6 | 3,5-dichloro-4-methylphenyl | $CH_2CH_3$ | $CH_3$ | 87 | 157–158 |
| 7 | phenyl | $CH_3$ | $CH_3$ | 74 | 154–155 |
| 8 | 1-ethylpentyl | $CH_3$ | $CH_3$ | 58 | 58–60 |
| 9 | 2-naphthyl | $CH_3$ | $CH_3$ | 60 | 151–152 |
| 10 | 3-pyridyl | $CH_3$ | $CH_3$ | 85 | 128 (decomp.) |
| 11 | 1,4-phenylene | $CH_2CH_3$ | $CH_2CH_3$ | 60 | 193–196 |

To further illustrate the benefits of the present invention by using TCIA as a chlorinating agent for 5-methyleneoxazolines, the following comparative examples were performed with other conventional chlorinating agents.

COMPARATIVE EXAMPLE C-1

Use of Chlorine Gas

A solution of 2-(3,5-dichloro-4-methylphenyl)-4-ethyl-4-methyl-5-methyleneoxazoline (20.0 g, 70.4 mmol) and methanol (100 mL) was cooled to 0° C. Chlorine gas was bubbled into the solution; the reaction was monitored by gas chromatography.([1]) The chlorine feed was halted when the starting material disappeared (1.5 h). The solution was purged with nitrogen to remove any remaining chlorine, then the solution was heated to 50° C. Water (20 mL) was added, and the reaction was stirred until hydrolysis was complete. The reaction mixture was cooled to room temperature, and the slurry was filtered. The wetcake was washed with cold solution of 10% water in methanol and dried in a vacuum oven to yield 15.89 g of white solid. The product contained 71% N-(1-chloro-3-methyl-2-oxopent-3-yl)-3,5-dichloro-4-methylbenzamide, 16% N-(1,1i-dichloro-3-methyl-2-oxopent-3-yl)-3,5-dichloro-4-methylbenzamide, and 0.8% N-(3-methyl-2-oxopent-3-yl)-3,5-dichloro-4-methylbenzamide. The yield of the desired monochloroketone was estimated at 48%. (Compare to Example C6).

([1]) NOTE WELL: Mixtures of chlorine gas and methanol can form methyl hypochlorite which is explosive and shock-sensitive.

COMPARATIVE EXAMPLE C-2

Use of N-Chlorosuccinimide

A solution of 2-(3,5-dichloro-4-methylphenyl)-4-ethyl-4-methyl-5-methyleneoxazoline (5.0 g, 17.6 mmol) and ethyl acetate (20 mL) was treated with N-chlorosuccinimide (2.35 g, 17.6 mmol). The solution was stirred at ambient temperature for 70 h. The reaction mixture contained 50% unreacted starting material and 50% of the desired 5-chloromethylene-2-(3,5-dichloro-4-methylphenyl)-4-ethyl-4-methyloxazoline. (Compare to Example C6).

It is to be understood that changes and variations in this invention may be made without departing from the spirit and scope of this invention as defined by the appended claims.

We claim:

1. A process for the preparation of a 5-methyleneoxazoline compound of formula (III) comprising cyclizing an alkynyl amido of formula (II) using an acid

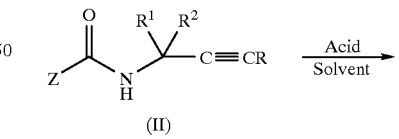

(II)

(III)

wherein

Z is alkyl or alkyl substituted with one or more substituents selected from the group consisting of alkoxy, halo, alkylthio and cyano; phenyl, naphthyl, or phenyl or naphthyl substituted with one to three substitutes independently selected from the group consisting of halo, alkyl, alkynyl, alkoxy, nitro or cyano; a 5-membered aromatic ring which may contain an oxygen atom, a sulfur atom, 1, 2 or 3 nitrogen atoms, an oxygen atom with 1 or 2 nitrogen atoms or a sulfur atom with 1 or 2 nitrogen atoms, or a 5-membered aromatic ring which may contain an oxygen atom, a sulfur atom, 1, 2 or 3 nitrogen atoms, an oxygen atom with 1 or 2 nitrogen atoms or a sulfur atom with 1 or 2 nitrogen atoms substituted with up to two substituents selected from halo, alkyl, haloalkyl or cyano; a 6-membered aromatic ring containing 1, 2 or 3 nitrogen atoms or a 6-membered aromatic ring containing 1, 2 or 3 nitrogen atoms substituted with up to two substitutes selected from halo, alkyl, haloalkyl or cyano; or phenylene, R is a hydrogen atom or alkyl, and $R^1$ and $R^2$ are each independently an alkyl or substituted alkyl group, or $R^1$ and $R^2$ together with the carbon atom to which they are attached form a cyclopentyl or cyclohexyl ring.

2. A process according to claim 1 wherein

Z is $(C_1-C_8)$alkyl, phenyl or phenyl substituted with up to three substituents independently selected from the group consisting of halo, $(C_1-C_4)$alkyl, $(C_1-C_4)$alkoxy, $(C_2-C_6)$alkynyl, nitro and cyano, 2-naphthyl, 3-pyridyl and 1,4-phenylene, R is a hydrogen atom or a $(C_1-C_4)$alkyl, and $R_1$ and $R^2$ are each independently a $(C_1-C_4)$alkyl or $R_1$ and $R^2$ together with the carbon atom to which they are attached form a cyclopentyl or cyclohexyl ring.

3. The process of claim 1 wherein

Z is 3-heptyl, phenyl, 4-halophenyl, 2,6-dihalophenyl, 4-$(C_1-C_4)$alkylphenyl, 3,5-dihalophenyl, 3,5-di$(C_1-C_4)$alkylphenyl, 4-$(C_1-C_4)$alkyl-3,5-dihalophenyl, 4-cyano-3,5-dihalophenyl, 4-$(C_1-C_4)$alkoxy-3,5-dihalophenyl, 4-nitrophenyl, 2-naphthyl, 3-pyridyl or 1,4-phenylene, R is a hydrogen atom, methyl or ethyl, and $R^1$ and $R^2$ are each independently methyl or ethyl or $R^1$ and $R^2$ together with the carbon atom to which they are attached form a cyclohexyl ring.

4. The process of claim 1 wherein

Z is 4-chlorophenyl, 2,6-difluorophenyl, 3,5-dimethylphenyl, 3,5-dichloro-4-methylphenyl, 4-nitrophenyl, 1,4-phenylene, 2-naphthyl, 3-pyridyl or 3-heptyl, R is a hydrogen atom, and $R^1$ and $R^2$ are each independently methyl or ethyl.

* * * * *